United States Patent
Carver et al.

(10) Patent No.: US 10,317,363 B2
(45) Date of Patent: *Jun. 11, 2019

(54) METHOD OF SCREENING SAMPLES

(71) Applicant: Micromass UK Limited, Wilmslow (GB)

(72) Inventors: Christopher Carver, Northwich (GB); David Eatough, Stockport (GB); Andrew Golding, Stockport (GB); Jeffrey Goshawk, Blackburn (GB); Michael McCullagh, Northwich (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/790,142

(22) Filed: Oct. 23, 2017

(65) Prior Publication Data
US 2018/0045679 A1   Feb. 15, 2018

Related U.S. Application Data

(63) Continuation of application No. 14/783,468, filed as application No. PCT/GB2014/051179 on Apr. 15, 2014, now Pat. No. 9,797,866.

(30) Foreign Application Priority Data

Apr. 15, 2013   (GB) .................................. 1306868.9

(51) Int. Cl.
*G01N 27/62*   (2006.01)
*H01J 49/00*   (2006.01)
*H01J 49/42*   (2006.01)

(52) U.S. Cl.
CPC ........ *G01N 27/622* (2013.01); *H01J 49/0031* (2013.01); *H01J 49/4215* (2013.01); *H01J 49/0045* (2013.01)

(58) Field of Classification Search
CPC ................ G01N 27/622; H01J 49/0031; H01J 49/4215; H01J 49/0045
USPC ................................ 250/281, 282, 286, 287
See application file for complete search history.

(56) References Cited

U.S. PATENT DOCUMENTS 8,822,914 B2 *  9/2014  Goshawk ............ H01J 49/0027
                                                250/281
9,797,866 B2 * 10/2017  Carver ................ H01J 49/0031

FOREIGN PATENT DOCUMENTS

WO   WO 2011/027131   *  3/2011   .............. H01J 49/00

* cited by examiner

*Primary Examiner* — Nicole M Ippolito
*Assistant Examiner* — Hanway Chang
(74) *Attorney, Agent, or Firm* — Womble Bond Dickinson (US) LLP; Deborah M. Vernon; Heath T. Misley

(57) ABSTRACT

A method of screening a sample for at least one compound of interest is disclosed. The method comprises comparing the ion mobility and at least one further physicochemical property of the ions of a compound of interest to the same properties of candidate ions in the sample. The properties of the compound of interest are matched to those of a candidate ion in the sample then the sample may be determined to comprise the compound of interest.

13 Claims, 8 Drawing Sheets

METHOD OF SCREENING SAMPLES

CROSS-REFERENCE TO RELATED APPLICATION

This application is a continuation of U.S. patent application Ser. No. 14/783,468, filed 9 Oct. 2015, which is the National Stage of International Application No. PCT/GB2014/051179, filed 15 Apr. 2014, which claims priority from and the benefit of United Kingdom patent application No. 1306868.9 filed on 15 Apr. 2013. The entire content of this application is incorporated herein by reference.

BACKGROUND OF THE PRESENT INVENTION

This invention relates generally to mass spectrometers and methods of their use and more specifically to mass spectrometers used for screening samples and methods of screening samples using mass spectrometers.

Often it is important to know if a component is present in a sample. Analysts may look for one or more components of interest that may only be present in trace amounts. One way of finding out if a component of interest is present in a sample is to analyse a sample using a liquid chromatography instrument coupled with a mass spectrometer (LCMS). The properties of the component of interest may then be searched against the corresponding properties of the ions detected by the spectrometer. For example, one may search the mass spectral data for candidate ions that have a retention time, mass and potentially fragment ion mass(es) that match the same properties of the ions of interest.

Each property is searched within a tolerance window. From one aspect it is desirable to set the tolerance window relatively wide so as not to exclude candidate ions that match the ions of interest. This is necessary because the value of an experimentally determined property may deviate from its true value due to experimental conditions. However, setting the tolerance window relatively wide also increases the likelihood of a large number of false positives being detected. From another aspect, it is desirable to set the tolerance window being relatively narrow, so as to avoid detecting false positives. A compromise must therefore be made when setting the width of each tolerance window, which may result in an increased likelihood of false positives and/or false negatives being detected.

Therefore, it is desired to provide a screening method which screens for known compounds, whilst reducing the number of false positives and false negatives that are detected.

SUMMARY OF THE PRESENT INVENTION

From a first aspect the present invention provides a method of screening a sample for at least one compound of interest comprising:

selecting at least one compound of interest that may be present in a sample and assigning an expected value, or range of expected values, corresponding to the ion mobility of the ions produced by ionisation of the compound of interest and an expected value, or range of expected values, of at least one further physicochemical property relating to the ions produced by ionisation of the compound of interest;

providing the sample to a mass spectrometer or ion mobility spectrometer;

ionising the sample to produce candidate ions;

experimentally measuring the ion mobilities of the candidate ions using an ion mobility separator so as to obtain an experimental value corresponding to the ion mobility of each of the candidate ions;

experimentally measuring said at least one further property relating to the candidate ions; and wherein, for each type of candidate ion, the experimental value corresponding to the ion mobility and said at least one further property are compared to the ion mobility value(s) and the at least one further property value(s) relating to the ions produced by ionisation of the compound of interest, respectively.

As described in the background of invention section above, conventional screening techniques must use a tolerance window of relatively small size when searching the properties of a compound of interest against the corresponding properties of candidate ions in experimentally obtained data, in order to avoid false positive detections. However, experimentally measured properties of ions may vary from their true values and so if the tolerance window is too narrow then the compound of interest may not be detected in the sample even if it is present.

The inventors of the present invention have recognised that the experimentally determined ion mobility of an ion is a particularly reproducible property and that it may therefore be used to overcome the above problems. In particular, the use of ion mobility in the screening process allows the tolerance window for this property to be relatively narrow, because the experimentally determined ion mobility does not deviate significantly from its true value. As such, many candidate ions that might otherwise provide false positive identifications can be excluded from being matches to the compound of interest. This enables the tolerance window for said at least one further physicochemical property to be made relatively wide. This is advantageous as said at least one further physicochemical property may be less experimentally reproducible than the ion mobility and so it may be important that the tolerance window for this property is set to be relatively wide in order to prevent false negatives being determined.

The ion mobility is preferably experimentally measured by experimentally measuring the drift times of the candidate ions through the ion mobility separator.

The method preferably comprises searching the expected value(s) of ion mobility against the experimentally measured values of ions mobilities for the candidate ions to determine matching values; and/or searching the expected value(s) of said further physicochemical property against the experimentally measured values of said further physicochemical property for the candidate ions to determine matching values.

This process of screening the sample by searching the properties of a predetermined compound of interest against the experimentally obtained properties of candidate ions in a sample is significantly more efficient than identification processes which search the experimentally measured properties of candidate ions against a list of properties of known ions in a database.

The method preferably comprises providing an ion mobility tolerance window that includes said expected value of ion mobility and that extends above and/or below said expected value of ion mobility; determining that any experimentally measured value of ion mobility for a candidate ion that is within said ion mobility tolerance window matches the ion mobility value of the compound of interest ion; providing a further property tolerance window that includes said expected value of the further physicochemical property and that extends above and/or below said expected value of the further physicochemical property; and determining that any experimentally measured value of the further physicochemical property for a candidate ion that is within said further property tolerance window matches the further physicochemical property value of the compound of interest ion. The ion mobility tolerance window may have a width that is x % of the expected value for the ion mobility of the compound of interest ion; the further property tolerance window may have a width that is y % of the expected value of the further physicochemical property; wherein x<y.

The value of x may be ≤5%, ≤10%, ≤20%, ≤30%, ≤40%, ≤50%, ≤60%, ≤70%, ≤80%, ≤90%, ≤95% or ≤99% of the value of y.

Preferably, if the expected value(s) of ion mobility and the expected value(s) of said at least one further physicochemical property match experimentally observed values of ion mobility and said at least one further physicochemical property for one of the candidate ions, then the compound of interest is determined to be within said sample, or said one of the candidate ions is subjected to further analysis.

Said at least one further property relating to the ions of the compound of interest preferably includes the mass of such ions, and said at least one further property relating to the candidate ions preferably includes the mass of such ions.

The method may further comprise fragmenting, reacting or activating the candidate ions to produce fragment or product ions, wherein the at least one further property relating to the candidate ions includes the mass of one or more of the fragment or product ions, and wherein said at least one further property relating to the compound of interest ions includes the mass of one or more of its fragment or product ions.

The method may comprise repeatedly and consecutively switching the method between a first mode and a second mode, wherein in the first mode the masses of the candidate ions are measured and in the second mode the candidate ions are fragmented, activated or reacted and the masses of the resulting candidate fragment or product ions are measured.

The mass of each candidate ion measured in each of the first modes may be associated with the mass(es) of its fragment or product ion(s) by associating a candidate ion measured in one of the first modes with its fragment or product ion(s) measured in the second mode that occurs immediately before or immediately after said first mode.

The method preferably alternates between the first and second modes at a rate such that each species of candidate ion is subjected to both of said first and second modes.

Preferably, the candidate ions are passed through said ion mobility separator prior to being mass analysed and/or fragmented.

The candidate ions may be transmitted from the ion mobility separator to a mass analyser that measures the masses of the candidate ions in the first mode, wherein the ion mobility separator varies the intensity profile of the candidate ions being transmitted to the mass analyser as a function of time so that different candidate ions are caused to have different intensity profiles as a function of time. The second mode may comprise fragmenting, activating or reacting the candidate ions so as to form fragment or product ions and mass analysing the fragment or product ions. The fragment or product ions may then be correlated with their corresponding candidate ions on the basis of the intensity profiles of said fragment or product ions and the intensity profiles of said candidate ions.

The mass of the precursor ion and the mass of its fragment/product ion may therefore be matched to the mass of a compound of interest ion and the mass of one or more of its fragment/product ions.

The sample provided to the spectrometer is preferably the eluent from a Liquid Chromatography separation device.

Said at least one further physicochemical property may include retention time in a chromatography device, wherein the retention times of the analytes that are ionised to form the candidate ions are recorded and compared to an expected retention time of the compound of interest, whereby if the retention time of the compound of interest matches a retention time associated with a candidate ion then the compound of interest is determined to be within said sample, or said one of the candidate ions is subjected to further analysis.

Then at least one further property relating to the compound of interest ions may include the isotopic pattern of the compound of interest ions, and said at least one further property relating to the candidate ions may include the isotopic pattern of the candidate ions.

Preferably, the isotopic pattern of the compound of interest ions is compared to the isotopic patterns of the candidate ions in order to determine if they match by: comparing the expected masses of the isotopes of the compound of interest ion to the experimentally determined masses of the isotopes of each candidate ion; and/or by comparing the relative intensities of the isotope peaks of the compound of interest ion with the relative intensities of the isotope peaks of each candidate ion. Multiple isotopes may be compared or monoisotopic peaks may be compared.

Alternatively, or additionally, to comparing the isotope patterns of the compound of interest ions and the candidate ions, the isotope patterns of their respective fragment ions may be compared in corresponding manner to that described above.

The identification of the at least one compound of interest may include the identification of candidate ions including at least one of a protomeric, isomeric, conformeric, or isobaric species.

The method may comprise determining that the compound of interest is in the sample and then quantifying the amount of the compound of interest in the sample.

Each of said at least one further physicochemical properties relating to the compound of interest ion that matches the corresponding property relating to a candidate ion (in addition to the ion mobility) increases the likelihood of the compound of interest being considered to be present in the sample.

The sample may be screened for a plurality of compounds of interests in the manner described herein.

From a second aspect the present invention provides a method of screening a sample for at least one compound of interest comprising:

selecting at least one compound of interest that may be present in a sample and assigning an expected value, or range of expected values, corresponding to the ion mobility of fragment or product ions produced by ionising and then fragmenting, reacting or activating the compound of interest; and assigning an expected value, or range of expected values, of at least one further physicochemical property relating to the fragment or product ions;

providing the sample to a mass spectrometer or ion mobility spectrometer;

ionising the sample to produce precursor ions;

fragmenting, activating or reacting the precursor ions to produce fragment or product ions;

experimentally measuring the ion mobilities of the fragment or product ions using an ion mobility separator so as to obtain an experimental value corresponding to the mobility of each of the fragment or product ions;

experimentally measuring at least one further property relating to the fragment or product ions;

wherein, for each type of fragment or product ion derived from the precursor ions, the experimental value corresponding to the ion mobility and said at least one further property are compared to the ion mobility value(s) and the at least one further property value(s) relating to the fragment or product ions of the compound of interest, respectively.

The method may comprise the features described in relation to the first aspect of the present invention, except wherein the features relate to the fragment or product ions of the compound of interest ions and the candidate ions, rather than to the compound of interest ions and the candidate ions themselves.

The present invention also provides an apparatus arranged and configured to perform the method described herein.

The present invention therefore provides an apparatus for screening a sample for at least one compound of interest comprising:

a memory for storing data relating to at least one compound of interest that may be present in a sample, including an expected value, or range of expected values, corresponding to the ion mobility of the ions produced by ionisation of the compound of interest and an expected value, or range of expected values, of at least one further physicochemical property relating to the ions produced by ionisation of the compound of interest;

an ion source for ionising the sample to produce candidate ions;

an ion mobility separator for experimentally measuring the ion mobilities of the candidate ions so as to obtain an experimental value corresponding to the ion mobility of each of the candidate ions;

means for experimentally measuring said at least one further property relating to the candidate ions; and processing means for comparing the experimental value corresponding to the ion mobility and said at least one further property for each type of candidate ion to the ion mobility value(s) and the at least one further property value(s) relating to the ions produced by ionisation of the compound of interest, respectively.

The present invention also provides an apparatus for screening a sample for at least one compound of interest comprising:

a memory for storing data relating to at least one compound of interest that may be present in a sample; including storing an expected value, or range of expected values, corresponding to the ion mobility of fragment or product ions produced by ionising and then fragmenting, reacting or activating the compound of interest; and for storing an expected value, or range of expected values, of at least one further physicochemical property relating to the fragment or product ions;

an ion source for ionising the sample to produce precursor ions;

means for fragmenting, activating or reacting the precursor ions to produce fragment or product ions;

an ion mobility separator for experimentally measuring the ion mobilities of the fragment or product ions so as to obtain an experimental value corresponding to the ion mobility of each of the fragment or product ions;

means for experimentally measuring said at least one further property relating to the fragment or product ions; and processing means for comparing the experimental value corresponding to the ion mobility and said at least one further property for each type of fragment or product ion derived from the precursor ions to the ion mobility value(s) and the at least one further property value(s) relating to the fragment or product ions of the compound of interest, respectively.

The present invention also provides a method of screening a sample comprising:— i) identifying at least one compound of interest that may be present in a sample and assigning an expected value corresponding to the mobility of the ions produced by ionisation of the compound of interest and an expected value of the at least one further property relating to the ions produced by ionisation of the compound of interest, ii) providing the sample to a mass spectrometer, iii) ionising the sample within the mass spectrometer to produce candidate ions, iv) measuring the drift time of the candidate ions through an ion mobility instrument to produce an experimental value corresponding to the mobility of the candidate ions, v) measuring at least one further property relating to the candidate ions in the mass spectrometer, vi) comparing the experimental value corresponding to the mobility of the candidate ions with an expected value corresponding to the mobility of the ions produced by ionisation of the compound of interest and the at least one further property relating to the candidate ions to an expected value of the at least one further property relating to the ions produced by ionisation of the compound of interest to confirm the presence of a compound of interest within the sample.

The one further property relating to the ions may include the mass of the candidate ions.

The method may further comprise fragmenting the candidate ions wherein the at least one further property relating to the ions may include the mass of the fragmented candidate ions.

The method may further comprise consecutively switching between a first mode and a second mode wherein in the first mode the mass of the candidate ions is measured and in the second mode the mass of fragmented candidate ions is measured.

The mass of the candidate ions and the mass of the fragmented candidate ions may be linked as originating from the same candidate ions according to the experimental value of the ion mobility of the candidate ions.

The sample provided to the mass spectrometer may be the eluent from a Liquid Chromatography separation. The retention time of the eluent provided to the mass spectrometer may be recorded and compared to an expected retention time of the compound of interest to further confirm the presence of a compound of interest within the sample.

The at least one further property relating to the ions may include the isotopic pattern of the candidate ions The at least one further property relating to the ions may include the isotopic pattern of the fragmented candidate ions The identification of the at least one compound of interest may include the identification of candidate ions including at least one of a protomeric, isomeric, conformeric, or isobaric species.

The present invention may include quantifying the amount of the at least one compound of interest if present in the sample.

The invention also provides a method of screening a sample comprising the steps of:— identifying at least one compound of interest that may be present in a sample, providing the sample to a mass spectrometer, ionising the sample within the mass spectrometer to produce candidate ions, fragmenting the candidate ions to produce fragment ions measuring the drift time of the fragment ions through an ion mobility instrument to produce an experimental value corresponding to the mobility of the fragment ions, measuring at least one further property relating to the fragment ions, and identifying the experimental value corresponding to the mobility of the fragment ions with an expected value corresponding to the mobility of the fragment ions and the at least one further a compound of interest to confirm the presence of a compound of interest within the sample.

The invention also provides an apparatus for the screening of a sample comprising providing:— a mass spectrometer having an ion source, an ion mobility separator, and a mass analyser arranged to provide an experimental value corresponding to the mobility of the candidate ion and at least one further property relating to the candidate ion, a sample potentially containing compounds of interest, a database comprising at least one compound of interest that may be present in the sample, containing an expected value corresponding to the mobility of the ions produced by ionisation of the compound of interest and an expected value of the at least one further property relating to the ions produced by ionisation of the compound of interest, and software for the comparison of the experimental value corresponding to the mobility of the candidate ions with an expected value corresponding to the ions produced by ionisation of the compound of interest and the at least one further experimental property relating to the candidate ions to an expected value of the at least one further theoretical property relating the ions produced by ionisation of the compound of interest to confirm the presence of a compound of interest within the sample.

It will be appreciated that when ion mass is referred to herein it refers to the mass to charge ratio of the ion.

The spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

Analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to a particularly preferred embodiment the process of Electron Transfer Dissociation fragmentation comprises interacting analyte ions with reagent ions, wherein the reagent ions comprise dicyanobenzene, 4-nitrotoluene or azulene reagent ions.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Figure 1:
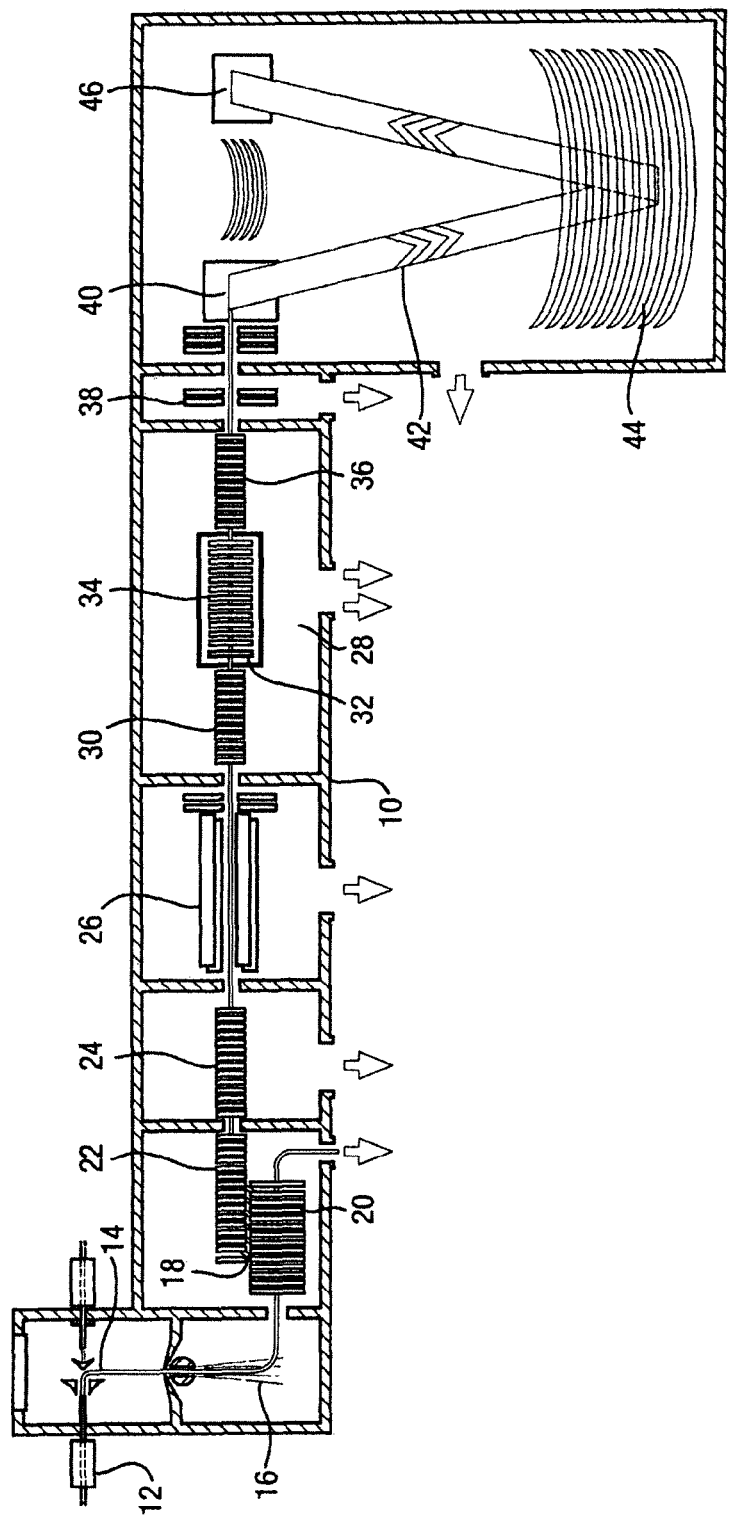
FIG. 1 shows an illustration of a mass spectrometer suitable for use with the invention.

FIG. 1 illustrates a mass spectrometer 10 suitable for use with the invention. When running, in this instrument, a sample is injected into the instrument at the injection inlet 12. The sample is sprayed from a needle into the ionisation chamber 14. Ionisation of the sample may occur, to form sample ions. The ionised sample will pass out of the ionisation chamber, and the ions will flow towards a first vacuum region 16. The will transfer through the first vacuum region, into the stepwave ion guide 18. The stepwave ion guide will then guide the ions along the ion guide initially in a large cross section area 20 and then, focus the ions into a smaller cross section in the off axis part 22 of the guide. The ions will then be transferred into a further ion guide 24, where the ions are transmitted through to a quadrupole mass filter 26.

The quadrupole mass filter can be used in a transmission mode, so that all the ions entering, pass through the filter, and passes into the Triwave chamber 28. Once the ions are passed into the Triwave chamber 28 they are collected in bunches within the trap cell 30 within the Triwave chamber 28. A bunch of ions in the trap cell, will then be released through the helium cell 32, into the ion mobility separator 34. The ions will then temporally separate according to their ion mobility within the mobility separator, and as ions exit the separator, they are passed into a transfer cell 36, where ions of small ranges of ion mobility are collected in groups, and passed through the transfer cell, several lenses 38 and into a ToF pusher region 40. Each group of ions of small mobility ranges can then be pulsed out of the ToF pusher region into a flight tube 42, into a reflectron 44, in where they are reflected back to a detection system 46, where the flight times of the ions are recorded, together with the small range of mobility of the ions.

A second, consecutive, analysis may then be performed along a similar basis, except, after the ions have been separated into the groups of small ranges of ion mobility in the separator 34, energy is provided to the ions within the transfer cell 36, to induce fragmentation of the ions in each group, to provide fragment ions. These fragment ions are kept in the small groups according to the mobility of the parent ions, and are passed into the ToF pusher region 40. Similarly, each group of fragment ions from the parent ions of small mobility ranges can then be pulsed out of the ToF pusher region into a flight tube 42, into a reflectron 44, in where they are reflected back to a detection system 46, where the flight times of these fragment ions are recorded, together with the small range of mobility of the parent ions that produced the fragment ions.

The information produced from each small mobility range in the first and the second analysis may be combined, to provide parent and fragment ion information for all the ions where the small range of mobility in the first and the second analysis matches.

In the preferred embodiment, once this data has been collected, the data can be interrogated by looking for each of the compounds of interest in the sample. The average collisional cross sectional area of each compound of interest can be determined, whether by mathematical calculation, or previous experiments, and calibration according to the conditions within the IMS device may occur. From this information, an expected drift time can be calculated for each compound of interest. This can be compared to the experimental data produced from the instrument, and, with a tolerance that can be set by a user, matches can be reviewed. Once the matches of the IMS value have been identified, the parent ion mass from the experimentally observed data (and/or daughter ion mass) can be compared to the expected mass of the compound of interest ion (and/or its daughter ions). If the expected mass(es) are present in the experimental data then there is a potential positive result to the screening experiment, which should be flagged for further investigation.

In the preferred embodiment, the compounds of interest may be a group of pesticides, which may or may not be present in a sample from a food stuff grown. In other embodiments the each compound of interest may be environmental contaminants in a sample taken form the environment. In a further embodiment the compounds of interest may be biological markers within a biological sample.

In the preferred embodiment the sample may be a food stuff for testing before being allowed into the food chain. In another embodiment the sample may be an environmental sample, for identifying contaminants within the environment. In a further embodiment the sample may be a biological sample being tested for the identification of disease. Other embodiments may include the sample being a natural product, a metabolite for identification, a compound where the purity is being analysed, a sample screened for toxins, an oil sample for grading, or a polymer sample for analysis.

The sample that is injected into the mass spectrometer may be the eluent from a Liquid Chromatography system. Where the sample injected into the mass spectrometer is the eluent from a Liquid Chromatography system, the retention time of the eluent is tracked, and checked against the expected retention time of the sample of interest as a further check on the properties of the match, compared to the compound of interest.

It would be apparent to the skilled person that the experimental values of the retention time of the compounds of interest may be affected by matrix effects, which may cause shifts in the values. The tolerances of the values of retention times may be set to try to allow for distortions due to matrix effects upon the retention time.

It would be apparent to the skilled person that the sample injected into the mass spectrometer need not be the product of a Liquid Chromatography run. In these embodiments the sample may be infused into the mass spectrometer, or the sample may be analysed using a direct ionisation technique.

The ion source used to ionise the sample may be any ion source. Examples of ion sources that may be used include, but are not limited to (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source, (xvi) a Nickel-63 radioactive ion source; (xvii) an Atmospheric Pressure Matrix Assisted Laser Desorption Ionisation ion source; (xviii) a Thermospray ion source; (xviiii) an atmospheric pressure solid analysis probe ion source (ASAP); and (xx) laser ablation with electrospray ionization (LAESI).

The mass spectrometer may be of any one of many different geometries.

The ion mobility device may be a drift tube, a travelling wave mobility device, an ion funnel ion mobility device, High-field asymmetric-waveform ion-mobility spectrometry (FAIMS) or one of any number of different Ion mobility measurement devices.

The mass analyser may be i) a Fourier Transform ("FT") mass analyser; (ii) a Fourier Transform Ion Cyclotron Resonance ("FTICR") mass analyser; (iii) a Time of Flight ("TOF") mass analyser; (iv) an orthogonal acceleration Time of Flight ("oaTOF") mass analyser; (v) an axial acceleration Time of Flight mass analyser; (vi) a magnetic sector mass spectrometer; (vii) a Paul or 3D quadrupole mass analyser; (viii) a 2D or linear quadrupole mass analyser; (ix) a Penning trap mass analyser; (x) an ion trap mass analyser; (xi) a Fourier Transform orbitrap, (xii) an electrostatic Fourier Transform mass spectrometer; and (xiii) a quadrupole mass analyser.

It would be apparent to the skilled person that the measure of ion mobility may be the drift time of the ions within the ion mobility device. In another embodiment the measure of ion mobility may be the 'time bin' that the ions are assigned to in the data, which should correspond to a range of ion mobilities. In a further embodiment the measure of ion mobility may be the collisional cross sectional area of the ions, which can be calculated from the drift time, and calibration according to the conditions in the ion mobility device. It would be apparent to the skilled person that any measure of intermediate value in this calculation may also be used.

The further property relating to the ions may be the accurate mass of the precursor ion, the accurate mass of a fragment ion, or the accurate mass of both the precursor ion and the fragment ion. Preferably, the accurate mass is a mass measurement to within ≤1 Da, ≤0.5 Da, ≤0.1 Da, ≤0.05 Da or ≤0.01 Da of the true mass. Alternatively, or additionally, one of the at least one further property relating to the ions may be the isotopic patterns that may be expected from the compound of interest, accurate mass of adduct ions, accurate mass of reaction products produced within the mass spectrometer, or accurate mass of reaction products produced prior to injection into the mass spectrometer In addition, the retention time may also be used to check for matches.

The use of more readings and known properties should lead to a reduction in the number of false positives. However, the more properties that are used for the matching, the more likely it is that a positive identification may be missed. It would be apparent to the skilled person that the experimental values may vary due to other reasons. For example, when using accurate mass, overlapping interfering peaks may lead to the distortion of the measurement of accurate mass, which would cause a shift of the peak, and an incorrect accurate mass. Similar issues may occur in the fragment ion mass. This would lead to a false negative result occurring.

The inventors have discovered that the use of ion mobility is particularly reproducible. Therefore, the inclusion of ion mobility in the screening process will allow for the tolerances of other values to be increased, so as to avoid false negatives, but also the values relating to the ion mobility should limit the number of false positives so as to reduce the time involved in the analysis of the data to provide positive confirmation of any positive detection of compounds of interest.

Preferably, when searching each of the physicochemical properties of the compound of interest ions against those that have been experimentally determined for the candidate ions, a tolerance window is used. Any experimental values for the candidate ions that fall within the tolerance window of the value for the compound of interest ion are determined to match the value of the compound of interest ion. As described above, the at least one further physicochemical property may include any one or any combination of: mass of precursor ions; mass of product or fragment ions; or retention time in a chromatography device.

The tolerance window for ion mobility may be set such that any candidate ion having an ion mobility value that is ≤w % above or below the value for the compound of interest is considered to be a match, wherein w may be: 0.1, 1, 2, 3, 4, or 5.

The tolerance window for mass may be set such that any parent candidate ion having a mass that is ≤x % above or below the parent mass for the compound of interest ion is considered to be a match, wherein x may be: 0.1, 1, 2, 3, 4, 5, 6, 7, 8, 9 or 10.

The tolerance window for mass may be set such that any fragment or product ion of a candidate ion having a mass that is ≤y % above or below the fragment or product ion of the compound of interest is considered to be a match, wherein y may be: 0.1, 1, 2, 3, 4, 5, 6, 7, 8, 9 or 10.

The tolerance window for retention time may be set such that any candidate ion whose analyte has a retention time that is ≤z % above or below the retention time for the compound of interest is considered to be a match, wherein z may be: 0.1, 1, 2, 3, 4, 5, 6, 7, 8, 9 or 10.

The at least one further physicochemical property may be potential protomers that may be possible when the compound of interest or candidate analyte ionizes. In this context, protomers are protonations of a molecule at different points on the molecule. The formation of protomers can vary dependent on the ionization conditions, so the appropriate conditions of ionization should be taken into account (or the same ionization conditions used). For example, different protomers may have different ion mobilities and so if a compound of interest is known to have one or more protomers the candidate ions can be searched for ion mobilities that match the corresponding one or more protomers.

Where there are protomers of the compound of interest, they are likely to have different collisional cross sectional areas, and hence different drift times through the ion mobility device. The detection of candidate ions having these drift times (or other ion mobility related properties) and having a mass measurement that matches the compound of interest ion can be used as a further confirmation of the presence of the compound of interest in the sample. This confirmation would not be possible without the use of ion mobility in the screening process.

The compound(s) of interest may be isomeric species. In these embodiments, the ion mobilities of the different isomers may be different and so if a compound of interest is known to have one or more isomers the candidate ions can be searched for ion mobilities that match the corresponding one or more isomers. It may be possible to identify the presence of one isomer, whilst confirming the presence and/or absence of another isomer. This may not be possible using conventional techniques. An example of this within the natural products/food analysis field may be isoorientin and orientin.

The compound(s) of interest may include several conformers. These are compounds of the same composition, but that have different shapes. The ion mobilities of different conformers may be different and so if a compound of interest is known to have one or more conformers the candidate ions can be searched for ion mobilities that match the corresponding one or more conformers. It may be possible to identify the presence of one conformer, whilst confirming the presence and/or absence of another conformer. This may not be possible using conventional techniques. An example of this would be that some sugars are conformers.

The compound(s) of interest may form ions that have the same accurate mass and the retention time, but different ion mobilities. In this case, by the separation using ion mobility, nominally isobaric and empirically isobaric species may be differentiated and identified. This may not be possible using conventional techniques. An example of this within the field of pesticide analysis may be triazophos and isazophos are nominally isobaric, and in the field of sugars analysis maltose and sucrose are empirically isobaric.

In addition to the screening according to the present invention, it may be possible to identify any unknown analyte detected in the analysis process from the data generated from the ion mobility separation and the other information provided by the mass spectrometer and/or liquid chromatograph, so that potentially unknown analytes can be assigned for future identifications.

The method may comprise, after the identification of the compound of interest within the sample, quantifying the amount of the compound of interest within the sample. This may be done by determining the peak area, the peak height, the ion intensity, the area of a mobility trace and the height of a mobility trace.

An example will now be described. Perfluorinated compounds (PFCs) are a class of man-made compounds that are frequently detected globally in biological and environmental samples. Perfluorooctane sulfonate (PFOS) is frequently detected in biological and environmental samples. MRM transition based LC-MS/MS analyses have been used previously to investigate PFOS in marine animals and human serum. Benskin et al. reported a common matrix interferent (taurodeoxycholate [TDCA]) that can complicate PFOS quantitation because it undergoes the same transition (499 m/z→80 m/z) and tends to co-elute with PFOS, giving a positive bias. The use of high definition mass spectrometry (HDMS) is explored as an important tool for unequivocal identification of PFOS isomers in environmental samples. This technique offers some unique advantages to profiling complex matrices.

The assay is based on the analysis of environmental sample extracts, mink liver and fish. These samples were injected on to a ultra performance liquid chromatography (UPLC) BEH $C_{18}$ (1.7 µm, 2.1×100 mm) analytical column. In addition a mixture of PFOS isomer solvent standards were injected on column. The chromatographic conditions were comprised of a 35 minute $H_2O$ (2 mM Ammonium Acetate) (A): 80:20 MeOH:ACN (B) gradient provided from a chromatographic system (equipped with PFC kit) operating at 0.45 ml/min and sample injection volumes of 5 µl used. Negative ion electrospray with ion mobility $MS^E$ data acquisition was performed using an Synapt G2-S HDMS mass spectrometer.

The results obtained to determine the presence of PFOS in mink, clearly show the benefits of using HDMS. It is possible to separate co-eluting analytes and increase the peak capacity using ion mobility. The PFOS isomers were resolved from the interfering components as they have vastly different mobility drift times. This approach negates the need for complex chromatography, extensive sample clean up or highly specific MS experimental design. All of the mass spectral information is retained, precursor and fragmentation information is acquired simultaneously and drift times enabling further characteristic profiling. With this information, it has been possible to create a characteristic assignment profile of PFOS isomers that co-elute with the cholic acid interferences. Using a prototype software platform, the target retention times were profiled to automatically generate the precursor and fragmentation spectra as well as the drift times for the identified PFOS isomers. The results obtained warrant further exploration into the use of ion mobility as an approach to confirming the presence of PFOS isomers in the environment where confidence can be had that no contribution from isobaric interference's is made.

In this example, resolution of isobaric interference's using ion mobility to identify and characterize PFOS isomers determined to be present in environmental samples has been performed.

A second example will now be described. Current trends indicate that more than 500 compounds are routinely used under strict regulation on a global basis. With increasing global trade there is a requirement for multi-analyte screening strategies capable of efficiently detecting residue violations to protect consumer safety. Benefits of full spectra acquisition and the specificity of accurate mass measurement is well characterised and is used in combination with, time tolerances, isotope fits, fragment ions/ratios and response thresholds to reduce false positive/negative identifications in screening assays. Nonetheless, it is a challenge to identify targeted compounds present in the sample with a large number of co-extracted matrix components. The application of ion mobility to remove false positive identifications and importantly false negative identifications, will be presented.

The assay is based on the analysis of sample extracts and matrix matched calibrants of pear, ginger, leek and mandarin, as well as quality control samples generated for an EU-RL proficiency test. These samples were injected on to ultra performance liquid chromatography (UPLC) BEH $C_{18}$ (1.7 µm, 2.1×100 mm) analytical column. In addition a series of mixtures of pesticide solvent standards were injected on column. The chromatographic conditions were comprised of a 15 minute water/methanol (0.005 m ammonium acetate) gradient at 0.45 ml/min and sample injection volumes of 5 μl were used. Positive ion electrospray with ion mobility $MS^E$ ($HDMS^E$) data acquisition was performed using a Synapt G2-S HDMS mass spectrometer.

UPLC $HDMS^E$ data was initially acquired for a series of solvent standard mixtures. These were utilized to generate mobility separated single component $MS^E$ spectra for the $[M+H]^+$ species. Thereby precursor ion, fragment ions and drift time was acquired for the pesticide standards. Subsequently the corresponding set of data was acquired for the pear, ginger, leek, mandarin matched matrix calibration series and then EU-RL proficiency test samples. The drift times generated from the solvent standards and the matrix matched calibrants were shown to statistically belong to the same population. Matrix-related retention time shifts have been determined and cross correlated to the drift time information obtained. Hence it can be shown that the drift time of the pesticide standards is independent of the matrix and can be utilized as a confirmatory parameter to increase confidence in identification and further reduce false positive and negative identifications. The use of drift time offers the potential to reduce the initial specificity of applied screening parameters. The drift time data generated was entered into a scientific library within a new scientific information system. This allowed the expected and determined drift times to be utilized to reduce false identifications in the proficiency test samples and matrix matched calibrant series analysed.

In this example, the use of ion mobility to reduce false positives and false negatives in screening methods for pesticide residues in food has been performed.

A further example will now be described. Fluoroquinolones are a class of antimicrobial agents which have been administered to livestock for different purposes, (a) prevention and control of infections and (b) growth promotion. Due to concerns regarding the spread of resistant microorganisms in the human population, the USA FDA introduced a ban on the use of enrofloxacin and ciprofloxacin in livestock production in 2005. Use of antibiotic growth promoting agents in animal husbandry has been forbidden in the EU since 2006. Here we report, use of High Definition Mass Spectrometry (HDMS) as a powerful tool for method development to support, unequivocal identification of fluoroquinolone antibiotic residues. Single component precursor ion and fragmentation spectra can be simultaneously acquired in a single HDMS experiment referred to as $HDMS^E$.

The assay is based on the analysis of porcine sample extracts and a mixture of veterinary drug solvent standards, containing fluoroquinolones, tetracyclines and macrolides. These samples were injected on to a ultra performance liquid chromatography (UPLC) BEH $C_{18}$ (1.7 μm, 2.1×50 mm) analytical column. The chromatographic conditions were comprised of a 9 minute water/acetonitrile (0.1% formic acid) gradient at 0.6 ml/min and sample injection volumes of 10 μl were used. Positive ion electrospray with $HDMS^E$ data acquisition was performed using a Synapt G2-S HDMS mass spectrometer.

Ultra performance liquid chromatography (UPLC) $HDMS^E$ data was initially acquired for a series of porcine extracts, solvent and standard mixtures of fluoroquinolones, tetracyclines and macrolides. These were utilized to generate mobility separated single component $MS^E$ spectra for the $[M+H]^+$ species, hence precursor ion, fragment ions and drift time were determined. The enhanced analytical performance facilitated the detection of antibiotics in a selection of sample types requiring only a simple and generic extract preparation step. HDMS can not only provide additional peak capacity but also new insights into the molecular characteristics of the analytes during the method development process. The data presented here shows the detection and elucidation of multiple sites of protonation within a single compound. Drift times of the veterinary drug standards are independent of the matrix and can be utilized as a confirmatory parameter to increase confidence in identification and further reduce false positive and negative identifications. The drift time data generated was entered into a scientific library within a prototype software platform, thus allowing the single component $MS^E$ spectra and drift times of each respective protonated site of the fluoroquinolones to be determined and characterized automatically. The presence of the multiple sites of protonation that were observed in this study, may account for variations seen in proficiency test results for these compounds. Ion mobility can be used as an investigative tool to fully understand the impact of the parameters employed in an analytical assay and on the results that can be obtained. Using this information, improved experimental designs can be employed to ensure more reliable and reproducible results.

In this example Ion mobility separation and structural characterization of isobaric species formed from the multiple sites of protonation for fluoroquinolone veterinary drugs has been performed.

Figure 2:
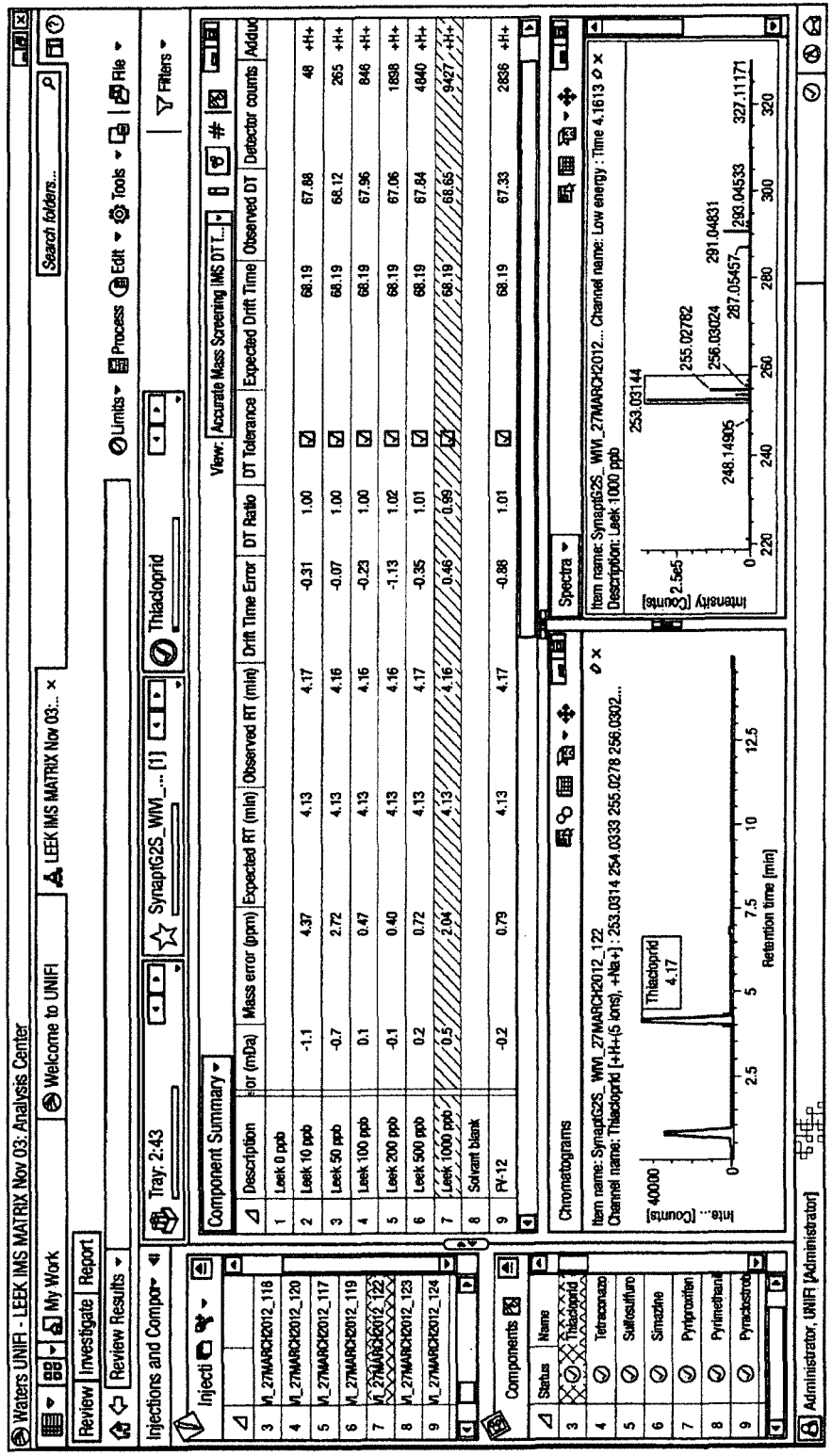
FIGS. 2-5 show screenshots of sets of results produced in accordance with an embodiment of the present invention.

FIG. 2 illustrates an extract of leek spiked with pesticides to form a matrix matched calibration series. The sample contains unknown pesticides. In conjunction with mass accuracy, retention time and the drift time observed for the identified pesticide, the data confirms Thiacloprid's presence in the unknown sample. The CCS/Drift time or drift bin has been used as an identification point to give added confidence.

Figure 3:
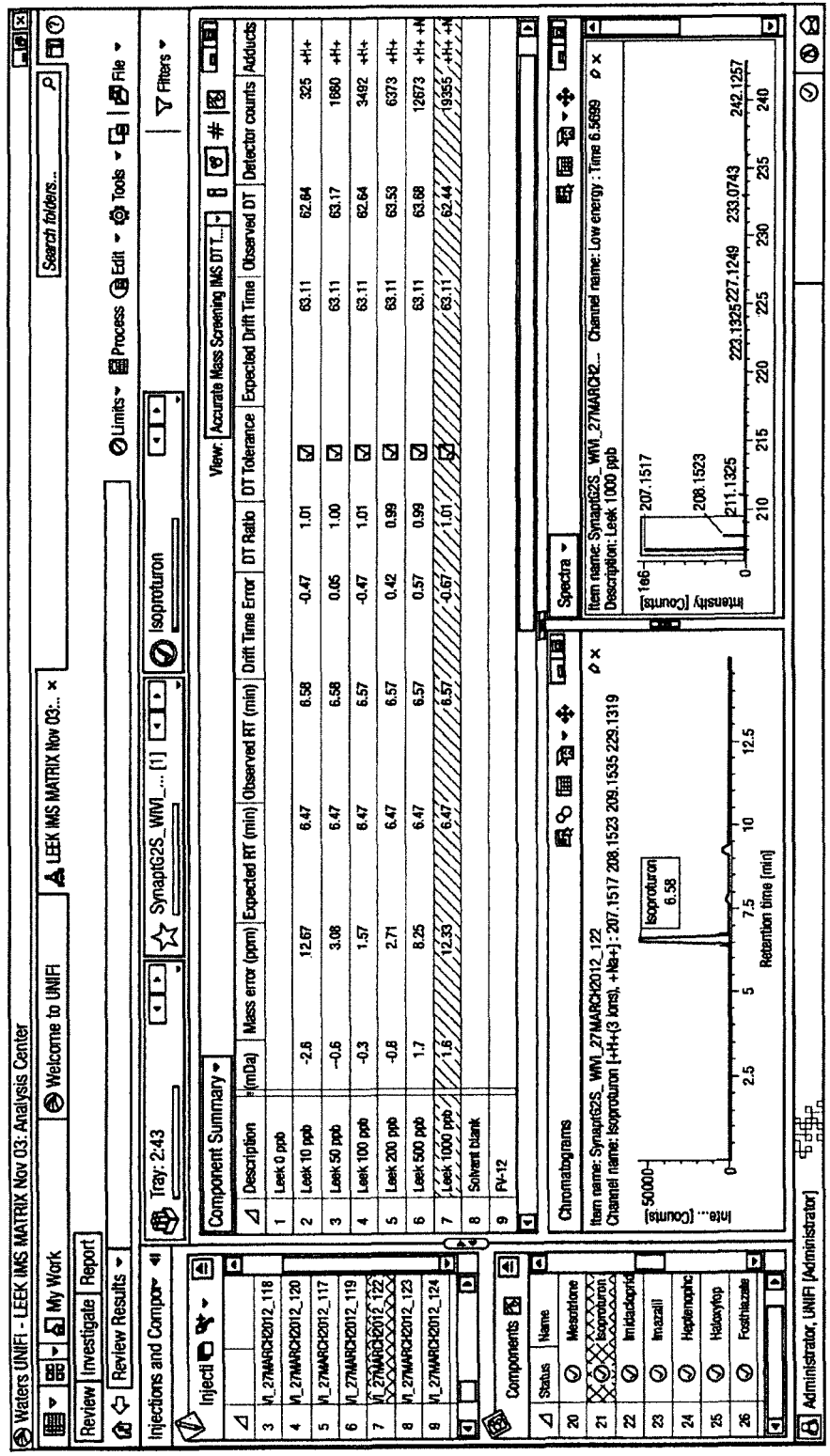

FIG. 3 illustrates an extracts of leek spiked with pesticides to form a matrix matched calibration series. The sample contains unknown pesticides. In conjunction with mass accuracy, retention time the drift time observed for the identified pesticide, further confirms Isoproturon's presence in the unknown sample. CCS/Drift time or drift bin has been used as an identification point to give added confidence. In this case it can be seen that for two points on the matrix matched calibration curve labelled at 1000 ppb and 10 ppb, the mass accuracy is >12 ppm. If a screening tolerance of less that 12 ppm had been used, the pesticide isoproturon would not have been identified. It is possible that the mass accuracy performance is not less than 5 ppm as typically expected, due to interference. But as a result of having the Drift time measurement, it has been possible to correctly identify isoproturon. In this case if typical screening parameters had been used i.e. 5 ppm mass accuracy tolerance, a false negative result would have occurred. Hence CCS, Drift time or Drift Bin can be used to reduce both false positive and false negative identifications.

Figure 4:
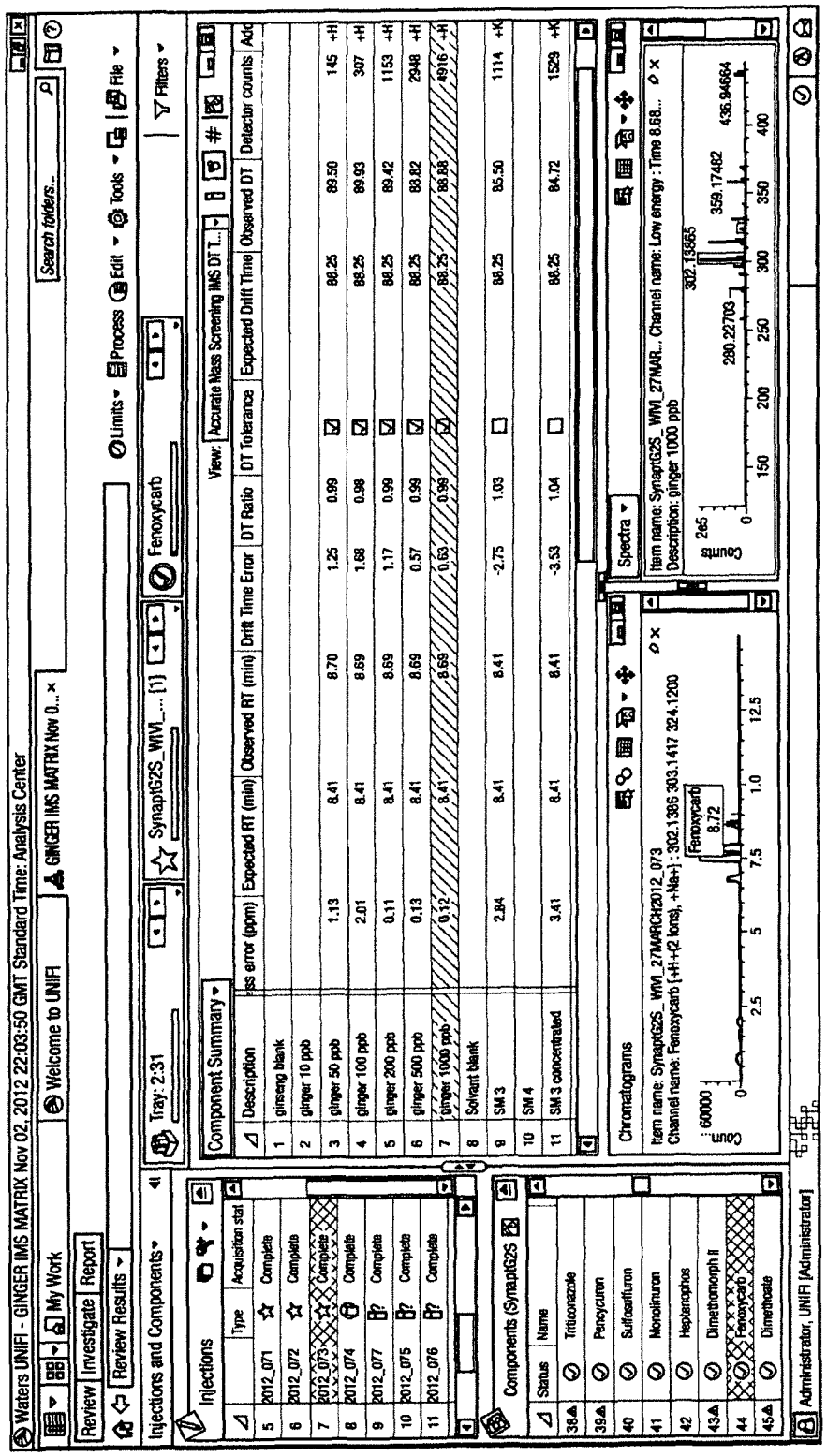

FIG. 4 illustrates an extracts of ginger spiked with pesticides to form a matrix matched calibration series. The sample contains unknown pesticides. In conjunction with mass accuracy and retention time, the drift time observed for the identified pesticide fenoxycarb has been identified to be present in the unknown sample. The retention time of fenoxycarb is 8.41 mins, exactly the same as the expected value. It can be seen that in the matrix matched calibration series, that the observed retention time for fenoxy carb is 8.69 mins. The observed drift times for the analyte identified in the matrix matched series also differ. The compound identified as being as fenoxycarb, is actually the K+ addict of another compound, which meets the retention time and accurate mass tolerances set. However the drift time tolerances are not met, and drift time has been used to show that a false positive identification has been made.

Figure 5:
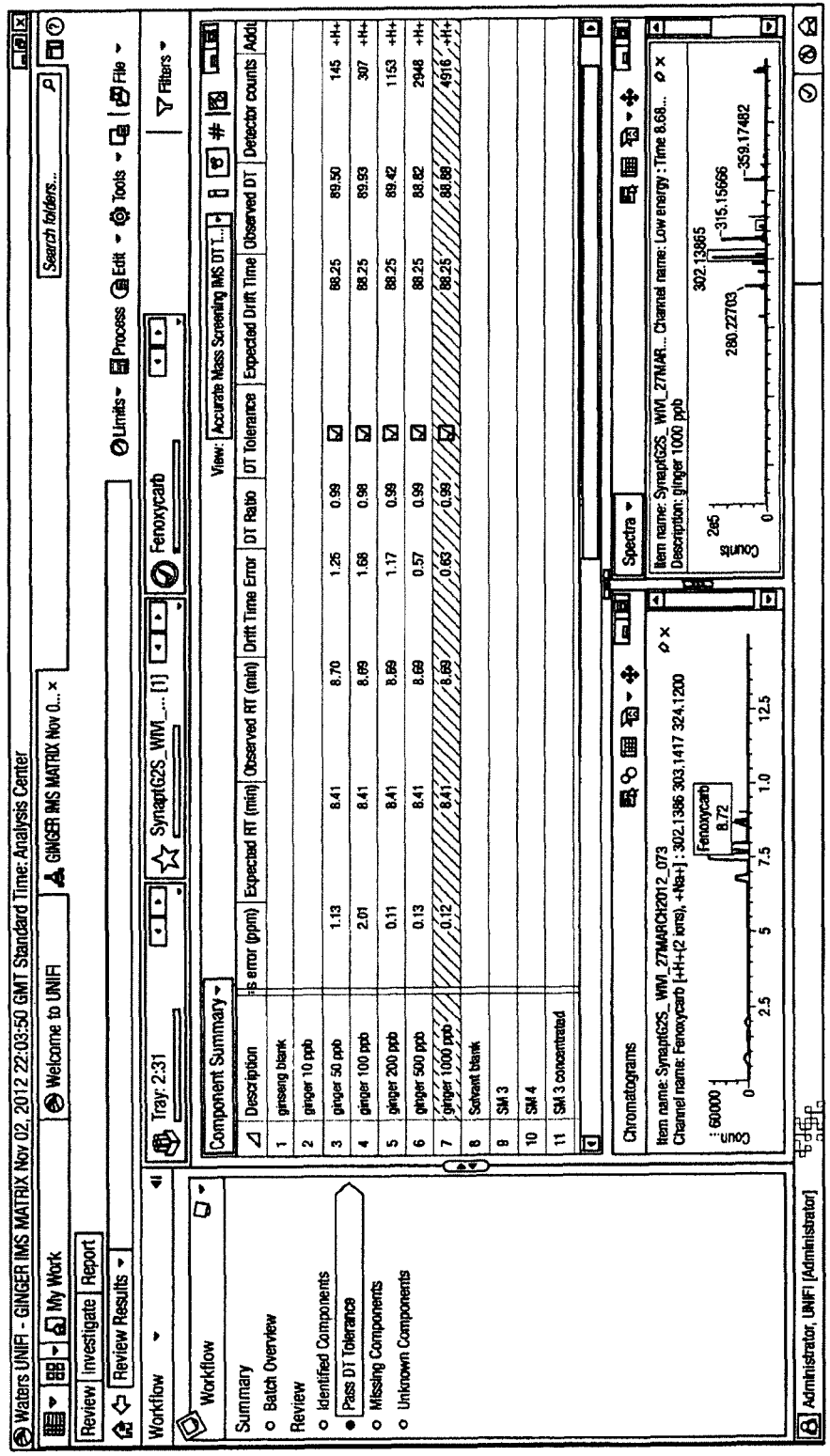

FIG. 5 illustrates that using a tolerance filter the false positive identification for fenoxycarb has been removed. This illustrates the ability to use drift time, drift bin or CCS as a means of reducing false positive identifications.

In the example in FIGS. 4 and 5, using prototype software a custom calculation was used to create a ratio of expected drift bin and the measured drift bin. If the ratio was 1.02 or 0.98, then the measurement achieved was within 2% of the expected drift bin value. The number of drift bins will equate to a drift time in milliseconds and from these measurements in conjunction with application of a mobility calibration, a collision cross section can be generated.

Figure 6:
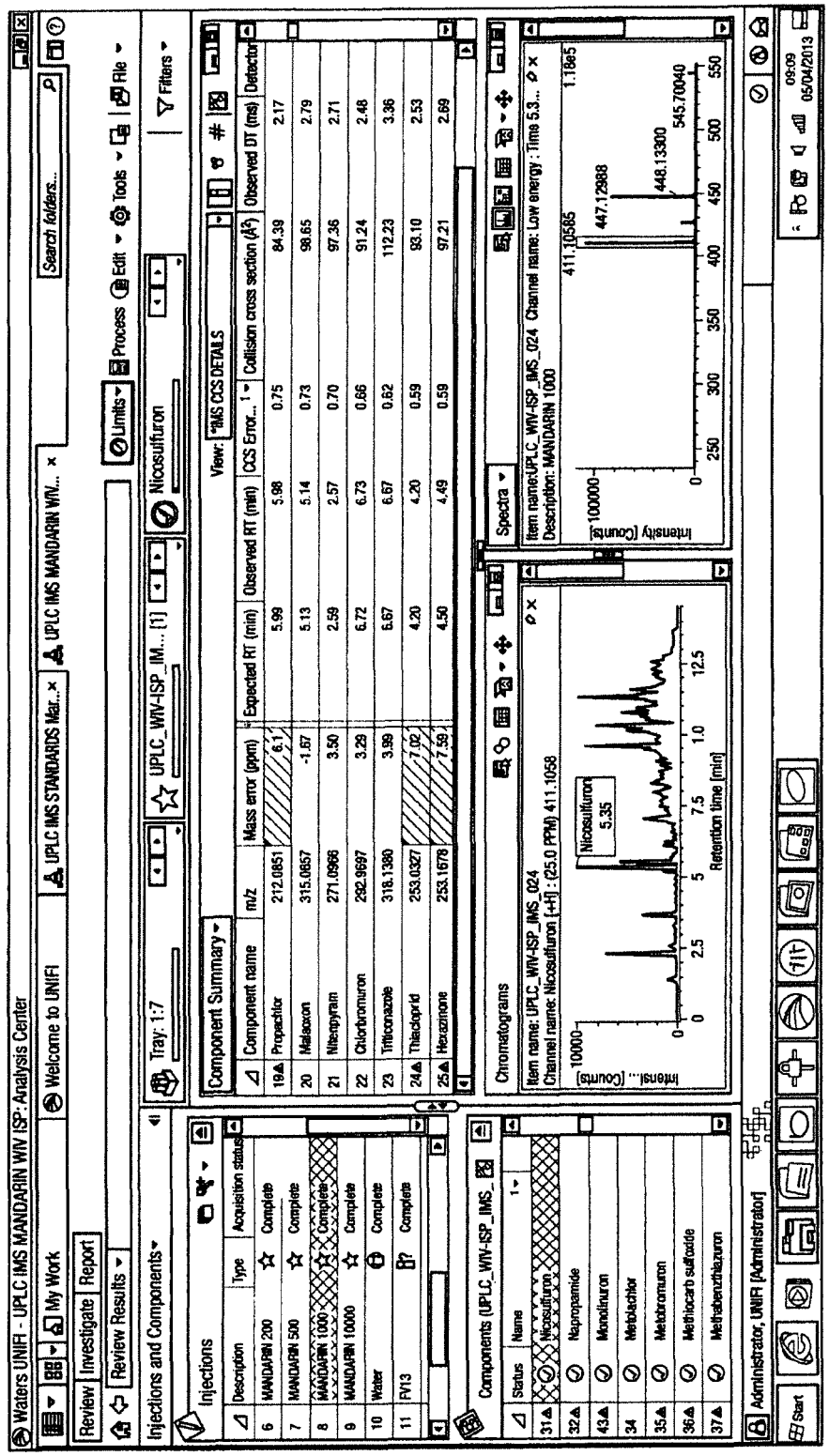
FIG. 6 shows a screenshot of a summary of results created in accordance with an embodiment of the present invention.

FIG. 6 is an illustration of use of average collision cross sections generated using travelling wave ion mobility to avoid false positive and false negative identifications.

In FIG. 6, the prototype build of software has been used to process a mandarin matrix sample spiked with known pesticides. The standard pesticides in solvent were used to generate the CCS value of each pesticide. These CCS values were entered into the scientific library. The mandarin matrix was screened for pesticides. It can be seen that the % error for the pesticides illustrated is within 2% of the expected CCS value. However several of the detected pesticides have greater than 5 ppm mass measurement error. If a mass measurement error of 5 ppm or less has be used to screen the data, these pesticides would not have identified within those tolerances and a false negative result would have occurred. The CCS tolerance allows confirmation of the correct identification despite mass measurement errors of >5 ppm being obtained.

In some embodiments the invention can be used to give an additional identification point. For examples in the Pesticides Residue screening studies 100 to 1000's of compounds can be screen for in complex matrices. The process of screening relies on known information and a library of targets is screened against non targeted data acquisitions. The libraries can utilize parameters such as precursor accurate mass, fragment ion accurate mass, retention time, ion ratio, isotope patterns and adduct information. In any assay involving complex matrices such as pesticide residue screening, veterinary drug screening and metabolite identification, the matrix being screened can cause problems such as sample suppression, retention time shifts and reduced mass accuracy due to the presence of matrix inferences at the target mass or due to ion statistics where low ion counts occur. These parameters are relied upon within applied tolerances to produce an identification. High numbers of false identifications can occur. CCS/Drift time/Drift bin measurements are independent of matrix, low ion statistics and retention time and can be used to reduce the number of false identifications/false negative identifications or confirm identification. These parameters can also be used to characterize unknowns.

Figure 7:
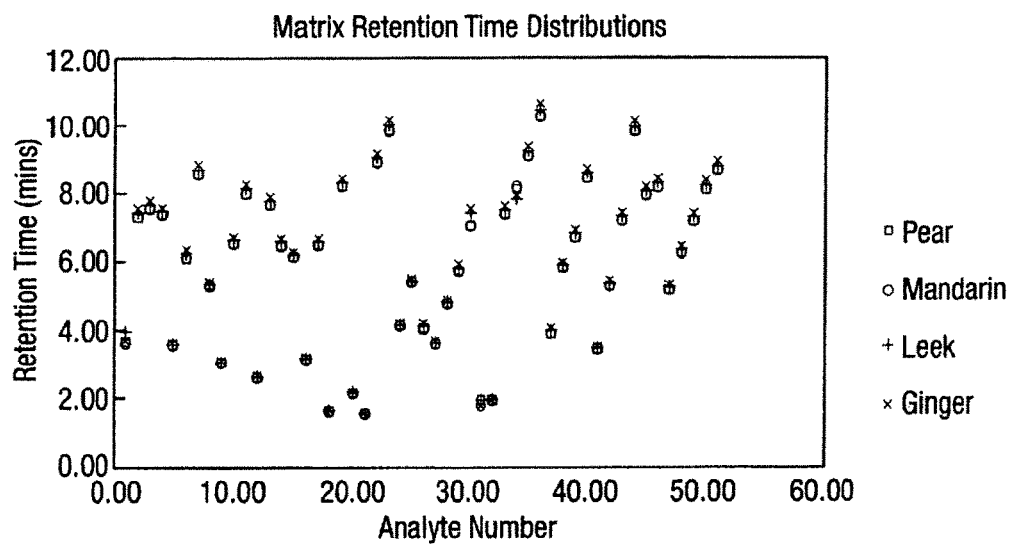
FIG. 7 is a graph of retention time variations, caused by different sample components.

FIG. 7 is a graph illustrating the effect of matrix on observed retention time, for a series of analytes. As can be seen form the graph, variations can be seen dependent upon the matrix that is present.

Figure 8:
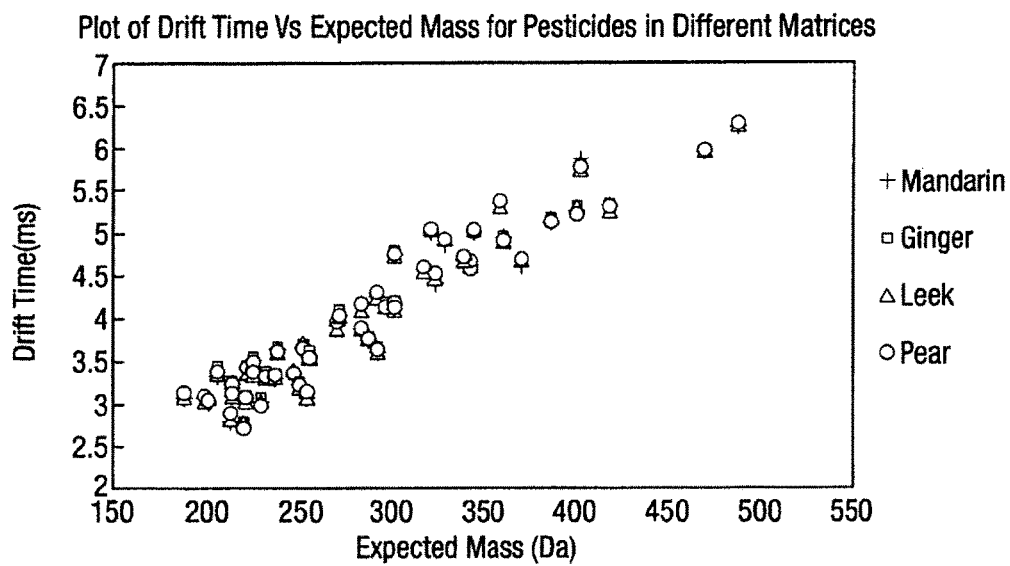
FIG. 8 is a graph of drift time variations, caused by different sample components.

FIG. 8 is a graph illustrating the effect of matrix on observed drift times. It can be seen that there is very little, or no observed shifts in determined drift time, and seems to be independent of the matrix.

Figure 9:
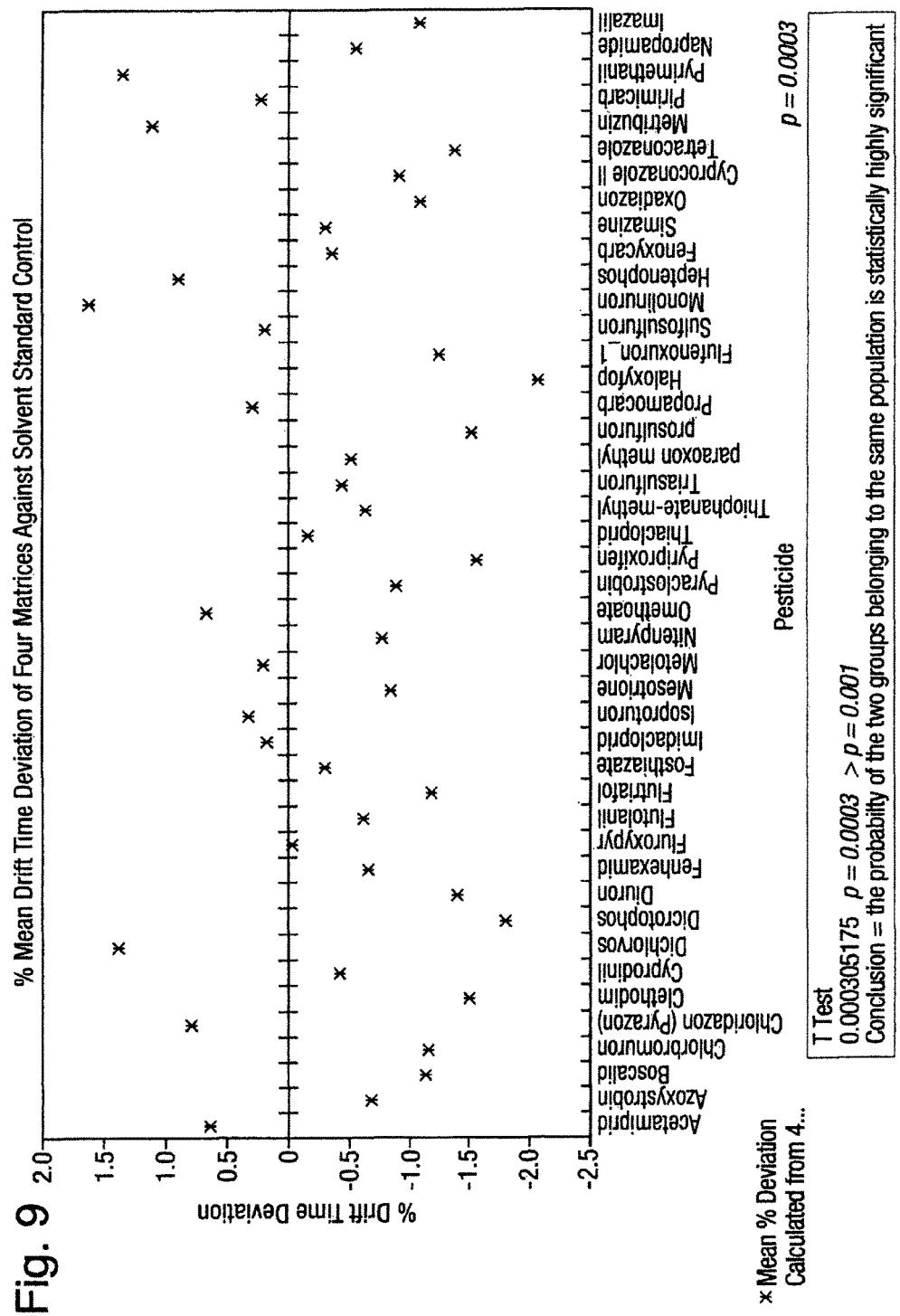
FIG. 9 is a graph showing the mean % deviation of drift time variation caused by different sample components.

FIG. 9 is a graph illustrating the % mean drift time deviation of the target analytes in four matrices against the drift times for the solvent standard controls. Using a one tailed t test it is statistically shown that there is a significant probability that the two groups belong to the same population and hence the drift time/drift bin/ccs measurements are independent of matrix. Therefore they can be used as an identification point.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry or ion mobility spectrometry comprising:
    separating a sample using a liquid chromatography device to produce a liquid chromatography eluent;
    ionizing the liquid chromatography eluent to produce candidate ions;
determining an experimental value of retention time in the liquid chromatography device corresponding to each of the candidate ions;
    experimentally measuring the ion mobilities of the candidate ions using an ion mobility separator so as to obtain an experimental value corresponding to the ion mobility of each of the candidate ions;
    experimentally measuring the mass to charge ratios of the candidate ions so as to obtain an experimental value corresponding to the mass to charge ratio of each of the candidate ions; and
    distinguishing candidate ions having substantially the same retention time and mass to charge ratio, but different ion mobility.

2. The method of claim 1, comprising experimentally measuring the mass to charge ratios of the candidate ions using a quadrupole mass analyser or a Time of Flight mass analyser.

3. The method of claim 1, further comprising fragmenting, reacting or activating the candidate ions to produce fragment or product ions.

4. The method of claim 3, further comprising repeatedly and consecutively switching the method between a first mode and a second mode, wherein in the first mode the mass to charge ratios of the candidate ions are measured and in the second mode the candidate ions are fragmented, activated or reacted and the mass to charge ratios of the resulting candidate fragment or product ions are measured.

5. The method of claim 4, wherein the method alternates between the first and second modes at a rate such that each species of candidate ion is subjected to both of said first and second modes.

6. The method of claim 4, wherein candidate ions are transmitted from the ion mobility separator to a mass analyser that measures the masses of the candidate ions in the first mode, wherein the ion mobility separator varies the intensity profile of the candidate ions being transmitted to the mass analyser as a function of time so that different candidate ions are caused to have different intensity profiles as a function of time; and
    wherein the second mode comprises fragmenting, activating or reacting the candidate ions so as to form fragment or product ions; mass analysing the fragment or product ions; and
    wherein the fragment or product ions are correlated with their corresponding candidate ions on the basis of the intensity profiles of said fragment or product ions and the intensity profiles of said candidate ions.

7. The method of claim 3, wherein the candidate ions are passed through said ion mobility separator prior to being mass analysed and/or fragmented.

8. The method of claim 1, wherein the candidate ions comprise at least one of a protomeric, isomeric, conformeric, or isobaric species.

9. The method of claim 1 further comprising quantifying the amount of a compound of interest in the sample corresponding to at least one candidate ion.

10. A method of performing a multiple reaction monitoring experiment, comprising the method of claim 1.

11. A method of screening a sample for at least one compound of interest, comprising the method of claim 1.

12. A method of mass spectrometry or ion mobility spectrometry comprising:
   separating a sample using a liquid chromatography device to produce a liquid chromatography eluent;
   ionising the liquid chromatography eluent to produce precursor ions;
   fragmenting, activating or reacting the precursor ions to produce fragment or product ions;
   determining an experimental value of retention time in the liquid chromatography device corresponding to each of the fragment or product ions;
   experimentally measuring the ion mobilities of the fragment or product ions using an ion mobility separator so as to obtain an experimental value corresponding to the mobility of each of the fragment or product ions;
   experimentally measuring the mass to charge ratios of the fragment or product ions so as to obtain an experimental value corresponding to the mass to charge ratio of each of the fragment or product ions; and
   distinguishing fragment or product ions having substantially the same retention time and mass to charge ratio, but different ion mobility.

13. A mass spectrometer or ion mobility spectrometer comprising:
   a liquid chromatography device configured to separate a sample to produce a liquid chromatography eluent; and
   an ion source configured to ionise the liquid chromatography eluent to produce candidate ions;
   wherein the spectrometer is configured to determine an experimental value of retention time in the liquid chromatography device corresponding to each of the candidate ions; the spectrometer further comprising:
   an ion mobility separator configured to experimentally measure the ion mobilities of the candidate ions so as to obtain an experimental value corresponding to the ion mobility of each of the candidate ions; and
   a mass analyser configured to experimentally measure the mass to charge ratios of the candidate ions so as to obtain an experimental value corresponding to the mass to charge ratio of each of the candidate ions;
   wherein the spectrometer is further configured to distinguish candidate ions having substantially the same retention time and mass to charge ratio, but different ion mobility.

* * * * *